US00PP26089P2

(12) United States Plant Patent
Falstad, III

(10) Patent No.: US PP26,089 P2
(45) Date of Patent: Nov. 17, 2015

(54) ***HIBISCUS* PLANT NAMED 'CHERRY CHEESECAKE'**

(50) Latin Name: ***Hibiscus* hybrid (L.)**
Varietal Denomination: Cherry Cheesecake

(71) Applicant: Clarence H. Falstad, III, Holland, MI (US)

(72) Inventor: Clarence H. Falstad, III, Holland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 176 days.

(21) Appl. No.: 13/998,773

(22) Filed: Dec. 4, 2013

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — June Hwu

(57) ABSTRACT

A new and distinct cultivar of winter-hardy herbaceous *Hibiscus* hybrid plant named 'Cherry Cheesecake' with branched upright habit, foliage of dark-green with a faint blush of purple-gray overlay, many large flat-faced flowers over a long season; flowers having a cherry-red eye, strong radiating veining and a blush at the petal tips of magenta on a faint pink to near white background.

1 Drawing Sheet

Botanical classification: *Hibiscus* hybrid (L.).
Variety denomination: 'Cherry Cheesecake'.

BACKGROUND AND ORIGIN OF THE PLANT

The present invention relates to the new and distinct, hardy, herbaceous, perennial *Hibiscus* plant, *Hibiscus* 'Cherry Cheesecake' hybridized by Clarence H. Falstad, III in the summer of 2009 at a nursery in Zeeland, Mich. The new plant, originally labeled #F9-34-01-09, is from a cross between a proprietary hybrid #F7-152-03 (not patented) as the female or pod parent times the proprietary seedling identified as #07-155-05 (not patented) as the male or pollen parent. Both parents have a complex mixture of species in them, most likely including at least the species: *moscheutos, coccineus* and *laevis*. *Hibiscus* 'Cherry Cheesecake' was first asexually propagated in 2011 by both stem cuttings and sterile tissue culture at the same nursery in Zeeland, Mich. The resultant asexually propagated plants have been found to be stable and true to type in successive generations of asexual reproduction.

BRIEF SUMMARY OF THE PLANT

*Hibiscus* 'Cherry Cheesecake' differs from its parents as well as all other hardy *Hibiscus* known to the applicant in many traits. The original parents are no longer available for comparison purpose. The foliage color of 'Cherry Cheesecake' is a dark green with a slight blush overlay of grayed purple on top. The foliage shape of 'Cherry Cheesecake' is variable, depending on the time of year and position on the stem. Most leaves are palmatifid or shallowly palmately lobed with some either young leaves or those on immature plants being palmately ovate to ovate. The flowers of 'Cherry Cheesecake' are nearly flat-faced with deep cherry-red eye and radiating magenta veins in the petals and with a very faint pink to nearly white background and a concentrated magenta apex. The most similar *Hibiscus* cultivars to 'Cherry Cheesecake' known to the applicant are: *Hibiscus* 'Turn of the Century' (not patented), *Hibiscus* 'Summer Storm' U.S. Plant Pat. No. 20,443, and *Hibiscus* 'Kopper King' U.S. Plant Pat. No. 10,793. Compared to 'Turn of the Century' the new plant has darker foliage with less pronounced dissection in the foliage, and the flower of 'Turn of the Century' is thinner in substance, lighter reddish pattern and veining more on only one lateral side of the petal rather than the blush congregated on the apex and veining throughout in the adaxial surface and toward the apex on the abaxial surfaces as in 'Cherry Cheesecake'. Both 'Kopper King' and 'Summer Storm' have darker foliage with more dissection to the lobes, and the flowers of each have a fading blush of pinkish magenta that is concentrated in the center and then gradually diminishes toward the apex. Both 'Kopper King' and 'Summer Storm' have less pigment in the veins and more pigment between the veins of the petals than 'Cherry Cheesecake' with 'Summer Storm' the greatest. The center eye of 'Kopper King' and 'Summer Storm' is not as deep a color giving 'Cherry Cheesecake' greater contrast between the base and the eye, veins and apex.

*Hibiscus* 'Cherry Cheesecake' is a unique hardy herbaceous perennial *Hibiscus* with the following combined traits:

1. Hardy herbaceous perennial, with multiple-stemmed, branched, upright habit.
2. Many flat-faced flowers over a prolonged season.
3. Ruffled flower petals with a large cherry-red eye and strong veining and apex of magenta on a very faint pink to near white background.
4. Variably-shaped foliage of dark green with blush of purple-gray overlay.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
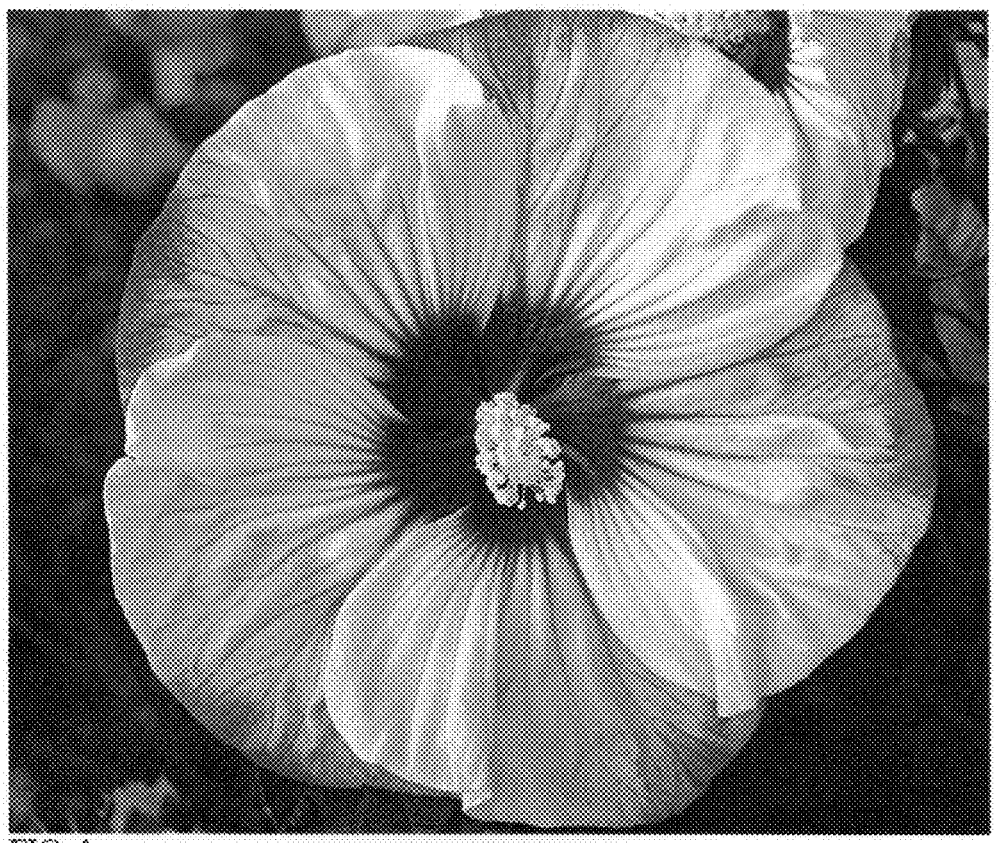
FIG. 1 shows a close-up of the flower with deep eye color, and veins and petal apex contrasting with the light background.
Figure 2:
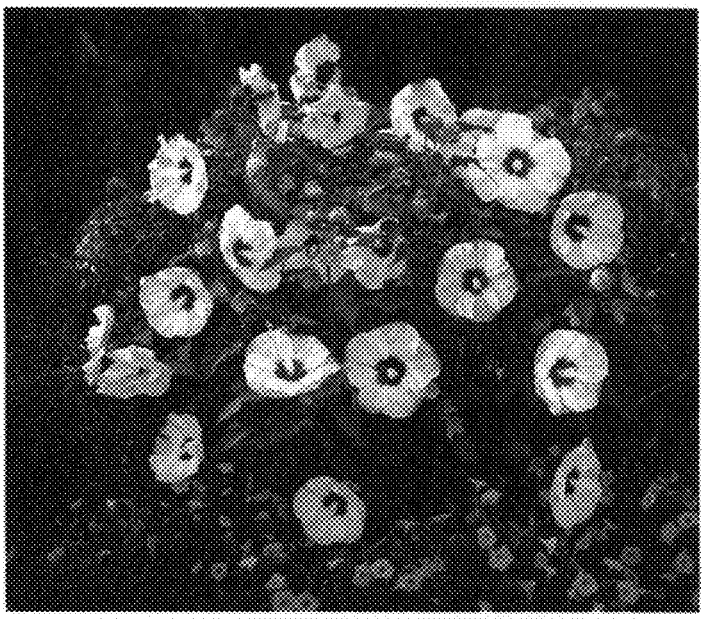
FIG. 2 shows the habit of a three year-old plant in mid-season flowering.

The following descriptions and color references are based on the 2001 edition of The Royal Horticultural Society Colour Chart except where common dictionary terms are used. The new plant, *Hibiscus* 'Cherry Cheesecake', has not been observed under all possible environments. The phenotype may vary slightly with different environmental conditions, such as temperature, light, fertility, moisture and maturity levels, but without any change in the genotype. The following observations and size descriptions are of three year-old plants in the loamy-sand open-sun field trials of a nursery in Zeeland, Mich. with supplemental fertilizer and water as needed. The plants are natural habit and were not treated with plant growth regulators, nor were they pinched at any time in the growth year.

Parentage: Proprietary seedling *Hibiscus* #F7-152-03 (not patented) as the female or pod parent times the proprietary seedling *Hibiscus* #07-155-05 (not patented) as the male or pollen parent.

Propagation:

*Method.*—Stem cuttings and sterile plant tissue culture division.

*Time to initiate roots from tissue culture.*—About two weeks.

*Rooting habit.*—Normal, branching, developing thick to about 3.0 cm diameter, fleshy; root color creamy white between RHS 159A and lighter than RHS 159 D depending on soil type.

*Crop time.*—Under normal summer growing conditions 12 to 16 weeks to flower in a four-liter container from cutting. Plant vigor is very good.

Plant description:

*Plant shape and habit.*—Hardy herbaceous perennial with about 16 thick upright and branched main stems producing an upright mound about 145 cm tall and 140.0 cm wide; 6 to 12 primary branches per main stem protruding at about 65° angle from horizontal, secondary branches on the lower one third to half of the primary branches; lateral branch size: between 8.0 cm and 40 cm long (shorter at the upper nodes) and average 1.0 cm diameter at the base of branch.

*Stem.*—Rounded, glabrous, glaucous; average about 130 cm tall and 2.5 cm diameter at the base.

*Stem color.*—Nearest RHS 147D.

*Plant size.*—Unpinched plant with stems about 145 cm tall; overall plant about 140.0 cm wide about ⅓ down from top (widest point).

*Internode.*—About 32 nodes per stem, average internode length about 4.5 cm of unpinched plant, varied between 2.5 to 7.5 cm, widest in middle portion of the stem.

*Foliage description.*—Alternate; dentate; glabrous; ovate to palmately tri-lobed with rounded to cordate bases and acute apexes; matte texture above and below; palmately veined.

*Leaf blade size.*—Up to 18.0 cm long and 18.0 cm wide, average 14 cm long and 11 cm wide, becoming smaller in distal portion of stem.

*Foliage color.*—Adaxial side RHS 139A with slight blushing of between RHS N187A and RHS N186C in unshaded bright sunlight; abaxial side between RHS N138C and RHS N138D.

*Veins.*—Palmate; primary and secondary adaxial vein color becoming reddish nearest RHS 187D in more light and RHS 185C in less direct sunlight; primary abaxial vein color more gray than RHS N144D and more yellow than RHS 138C with those leaves in more direct sunlight having tinting in the distal two thirds region of the leaf blade of nearest RHS 187D.

*Petioles.*—Glaucous, glabrous; nearly cylindrical with slight flattening on top surface; average size 6.0 cm long and 3.0 mm wide at the base.

*Petiole color.*—Above between RHS 139C and RHS 138B with tinting between RHS 183B and RHS N186C concentrated in areas of more light; at base and where protected from light between RHS 138A and RHS 138B; below nearest RHS 144A.

Flower description:

*Buds.*—One day prior to opening about 7.0 cm long and 4.5 cm in diameter, apex rounded with petals not joined at tips; base bluntly rounded, unopened petals wrinkled at veins, exposed petal color nearest RHS N186B with raised veins lighter purple nearest RHS 187B.

*Buds prior to showing colored petals.*—About 3.0 cm long and 2.5 cm in diameter, ovoid with acute apex, carinate at the fusion seam of the sepals; color between RHS 146D and RHS 147C with veins and sepal carina between RHS 137C and RHS 146C.

*Epicalyx.*—Entire, smooth, glabrous, linear with sharply acute apex and attenuate base, curved around sepals; 11 to 12 per flower; about 2.2 cm long tapering to base of about 2.5 mm wide; adaxial and abaxial color nearest RHS 146C.

*Sepals.*—Five, proximal half connate forming campanulate star-shaped calyx; acute apex; margin entire, edentate; individually about 4.2 cm long and 2.0 cm across, forming a corolla about 4.0 cm long and 5.0 cm diameter; adaxial color more yellow than RHS 147C, abaxial color darker green than RHS 144A; five primary sepal veins on abaxial surface same color as surrounding tissue and on adaxial surface between RHS 144D and RHS N144D.

*Flowers.*—Solitary, 16 to 22 per main stem without pinching; slightly cupped petals opening to about 170 degrees; upward and outwardly facing; about 23.0 cm across and 4.5 cm deep in center, larger in early part of flowering season; persist for a one to two days; effective for at least 12 weeks beginning mid-July and continuing into October; no detectable fragrance.

*Petals.*—Five; glabrous, slightly lustrous in center and matte in outer one half to two thirds on both adaxial and abaxial sides; adnate to the androecium, imbricate to about 100% overlapping at widest part (petals on either side overlapping above and below completely to the next petal two over); veins ribbed on back and impressed on front; frequently with one or more slight longitudinal crimping, folding or doubling over section, to about 1.0 cm wide, running the outer ⅔'s of petal providing additional strength and support for wind resistance; shape rounded; margins entire, edentate; apex rounded; base short claw-like; size: average 12.0 cm long and 13.0 cm wide at widest portion narrowing to a base about 8.0 mm wide (larger in earlier part of flowering season and smaller in later season); heavily pigmented veins radiating from darker eye that is about 6.0 cm in diameter; veins about 3.0 mm across toward center and diminishing to about 1.0 mm across toward apex and extend on adaxial side from eye all the way to the tip in the middle portion of the petal and in less and varying dimension in the petals farther away from the center; vein coloration on the abaxial side radiate from the apex and extend about 2.5 to 3.5 cm from the margin with the longest colored veins in the center of the petal.

*Petal color.*—Adaxial eye nearest RHS 53C in centermost 1.0 cm transitioning to between RHS 59A and RHS 187B for the next 2.0 cm before lightening to between RHS 53B and RHS 53C in the distal 2 to 3 mm; abaxial eye nearest RHS N155D; adaxial petal center portion near white to faint pink lighter than RHS N155D; abaxial center portion color near white to faint pink, lighter than RHS N155D; adaxial veins radiating from center eye between RHS 64 A and RHS 64B in the proximal 0.5 cm then becoming less saturated, nearest RHS 71C and RHS 71D and the veins become thinner extending toward apex; adaxial side with a concentrated blush of between RHS 64B and RHS 64C at the apex or slightly to the counter-clockwise side of the apex extending about 5.0 to 7.0 cm around margin and 1.5 cm thick; abaxial apex with a concentrated blush of between RHS 64B and RHS 64C slightly to the counter-clockwise side about 5.0 to 7.0 cm around margin and about 3.0 cm thick; vein coloration on the abaxial side radiate and is more concentrated at the apex rather than the base of the petal and is nearest RHS 64A near the apex and lightens to nearest RHS 64D before quickly blending with the rest of the abaxial near white to faint pink lighter than RHS N155D.

*Gynoecium.*—Style: enclosed in column about 4.5 cm long and 8.0 mm wide at base; column color nearest RHS 46C at base and lightening within 2 to 4 mm to more near white, lighter than RHS 155D distally; style protruding from column about 2.0 cm and split in distal 1.0 cm portion into five branches, branch diameter 2.0 mm; style color branch near white, lighter than RHS 155D; Stigma: five; globose, puberulose, about 2.0 mm in diameter, nearest RHS 158C; Ovary: superior, about 10.0 mm across at base and 8.0 mm tall; acute apex; color: closest to RHS 154D.

*Androecium.*—Filaments: numerous, about 120; less than 1.0 mm in diameter and about 5.0 mm long; attached to nearly the entire length of column; color near white nearest RHS 155D; Anthers: reniform; about 2.0 mm long and 1.5 mm wide; lighter than RHS 155D; Pollen: numerous, globose, less than 0.1 mm long, color nearest RHS 155D.

*Pedicel.*—Rounded, glabrous, from base of sepal to abscission point average 2.5 cm long and 3.0 mm wide on early flowers decreasing in distal flowers; color between RHS 146D and RHS 147C.

*Peduncle.*—Rounded, glabrous, flowers are held easily visible on average 4.5 cm long from abscission point to stem and 3.0 mm wide, longer on earlier flowers; base color between RHS 146C and RHS 147C.

*Fruit.*—Few, loculicidal capsule; glabrous; globose, occasionally with abruptly acute apex; RHS N199B when mature.

*Seed.*—Minutely floccose, globose to slightly reniform; 3 to 4 mm in diameter; color nearest RHS 200A.

Disease resistance: Resistance beyond that of other hardy *Hibiscus* cultivars has not been observed. The plant grows best with plenty of moisture and adequate drainage, but is able to tolerate some drought when mature. Flowers are resistant to harsh sun and stand up well to moderate winds and harsh rain with the folding of the petals. Hardiness at least from USDA zone 4 through 9, and other disease resistance is typical of that of other hardy *Hibiscus* cultivars.

I claim:

1. A new cultivar of hardy herbaceous *Hibiscus* hybrid plant named 'Cherry Cheesecake' as herein illustrated and described, with branched upright habit; also dark-green leaves with a faint blush of purple-gray overlay, many large flat-faced flowers over a long season; flowers having a cherry-red eye, strong radiating veining and a blush at the petal tips of magenta on a faint pink to near white background, suitable for potted plant culture, landscaping as a specimen or en masse.

* * * * *